United States Patent

Riveron et al.

[11] 4,209,517
[45] Jun. 24, 1980

[54] α-ETHYLENIC ALCOHOLS AND KETONES, THEIR PREPARATION, AND THEIR USE AS MEDICAMENTS

[75] Inventors: André M. Riveron, Seine-Saint-Denis; Jacques N. Astoin, Paris; Alain D. Marivain, Colombes; Micheline Crucifix born Dexheimer, Creteil; Martine M. Lapotre, Maisons-Alfort; Yvette M. Torrens born Le Gargean, La Frette-sur-Seine, all of France

[73] Assignee: Unicler, Paris, France

[21] Appl. No.: 925,211

[22] Filed: Jul. 17, 1978

[51] Int. Cl.² ........................................... C07D 407/02
[52] U.S. Cl. .................... 424/248.57; 260/340.5 R; 424/282; 424/250; 424/269; 542/400; 542/429; 542/439
[58] Field of Search ............... 260/340.5; 424/282, 424/248.57, 250, 267; 542/400, 439, 429

[56] References Cited

U.S. PATENT DOCUMENTS

| | | | |
|---|---|---|---|
| 2,452,188 | 10/1948 | Hedenburg | 260/340.5 R |
| 3,878,200 | 4/1975 | Diana et al. | 260/340.5 |
| 3,910,959 | 10/1975 | Vallet | 260/340.5 |
| 3,940,487 | 2/1976 | La Croix et al. | 260/340.5 R |

OTHER PUBLICATIONS

Zaidler et al., Chem. Abst. 64(1966), 14790e.
Unicler Chem. Abst. 84(1976) #89825.
Guozdjakova et al., Acta Facul. Rerum. Nature, Alniv. Com. Chim. 1971, pp. 25–31.
Synerholm et al., Contrib. Boyce Thompson Inst., 1945, pp. 79–80.
Synerholm et al., Contrib. Boyce Thompson Inst., 1945, pp. 433–434.

*Primary Examiner*—Arthur P. Demers
*Attorney, Agent, or Firm*—Stevens, Davis, Miller & Mosher

[57] ABSTRACT

The invention provides new compounds of the formula

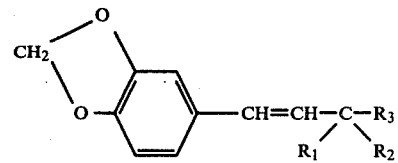

in which one of the symbols $R_1$ and $R_2$ denoted a hydrogen atom and the other a hydroxyl group or, together, the two denote an oxygen atom, and $R_3$ denotes an alkenyl group having 3 to 6 carbon atoms, a cyclohexyl group, or an aminoalkyl group in which the alkyl group has from 1 to 3 carbon atoms and the amino group is a morpholino, 4-methylpiperazino or piperidino radical, as well as the pharmaceutically acceptable addition salts of the compounds containing an amino group, which are useful as tranquilizers, anticonvulsants and antidepressants.

5 Claims, No Drawings

α-ETHYLENIC ALCOHOLS AND KETONES, THEIR PREPARATION, AND THEIR USE AS MEDICAMENTS

The object of the present invention are α-ethylenic alcohols and ketones, their preparation, and their use as medicaments.

U.S. Pat. No. 3,910,959 relates to 1-(3,4-methylenedioxyphenyl)-4,4-dimethyl-1-pentene-3-one and 1-(3,4-methylenedioxyphenyl)-4,4-dimethyl-1-pentene-3-ol, that can be used as medicaments.

The compounds of the invention have the formula

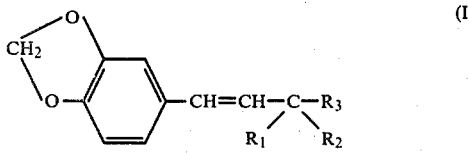

in which
one of the symbols $R_1$ and $R_2$ denotes a hydrogen atom and the other denotes a hydroxyl group or, together, the two denote an oxygen atom, and $R_3$ denotes an alkenyl group having 3 to 6 carbon atoms, a cyclohexyl group, or an aminoalkyl group in which the alkyl group has from 1 to 3 carbon atoms and the amino group is a morpholino, 4-methylpiperazino or piperidino radical, as well as the pharmaceutically acceptable addition salts of the compounds containing an amino group.

The compounds may be prepared by condensing, in an aqueous or alcoholic medium and in equimolecular amounts, the piperonal of formula

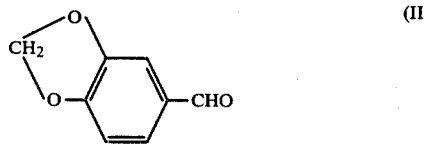

with a ketone of formula $R_3$-CO-CH$_3$ (III) in which formula $R_3$ has the meaning given above.

An α-ethylenic ketone of the formula

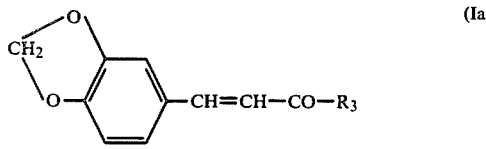

is thus obtained.

In order to obtain the corresponding α-ethylenic alcohol of the formula

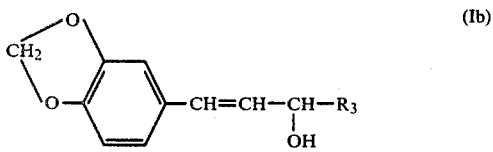

the ketone (Ia) is reduced, for example by means of potassium or sodium borohydride in an alcoholic medium. $R_3$ has the same meaning as in formula (I).

In order to prepare the compounds containing an amino group, the following method may advantageously be used. The organo-magnesium reagent of 3,4-methylenedioxyphenylacetylene is prepared and reacted with a nitrile $R'_3$—C≡N. After hydrolysis, an α-acetylenic ketone is obtained which may be reduced to the α-ethylenic ketone or corresponding alcohol, for example by means of LiAlH$_4$.

The following examples illustrate the preparation of the compounds of the invention.

EXAMPLE 1

1-(3,4-methylenedioxyphenyl)-4-morpholino-1-butene-3-one (Code No.: 996)

15 g of piperonal (0.1 mole), and 14.3 g of 3-morpholinoacetone (0.1 mole) are mixed in an aqueous-alcoholic sodium hydroxide solution (300 cm³ of 10% NaOH and 30 cm³ of ethanol). The mixture is stirred for 4 hours and the product obtained is then filtered. The product is rinsed with water and recrystallised from ethanol.

M.P.=105°, Yield 70%.

EXAMPLE 2

1-(3,4-methylenedioxyphenyl)-4-morpholino-1-butene-3-ol (Code No.: 997)

27.5 g of the ketone (0.1 M) obtained in Example 1 is dissolved in 300 cm³ of methanol and an aqueous solution of KBH$_4$ is added dropwise. The reaction mixture is left overnight and decomposed with water. The product obtained is filtered and recrystallised in ethanol.

M.P.=108°, Yield 85%.

EXAMPLE 3

1-(3,4-methylenedioxyphenyl)-7-methyl-1,6-octadiene-3-one (Code No.: 998)

15 g of piperonal (0.1 mole) and 12.6 g of 6-methyl-5-heptene-2-one (0.1 mole) in an aqueous-alcoholic solution of sodium hydroxide (200 cm³ of 10% NaOH +20 cm³ of ethanol) are stirred for 15 days at ambient temperature. The product obtained is filtered off, washed with water, and recrystallised from ethanol.

M.P.=66°, Yield 63%.

EXAMPLE 4

1-(3,4-methylenedioxyphenyl)-7-methyl-1,6-octadiene-3-ol (Code No.: 999)

The ketone obtained according to Example 3 above is used as starting material and the same technique as described in Example 2 is employed, with the exception that extraction is carried out with chloroform. Recrystallisation from petroleum ether.

M.P.=52°, Yield 78%.

EXAMPLE 5

1-(3,4-methylenedioxyphenyl)-4-methyl-5-morpholino-1-pentene-3-one (Code No.: 1156 b).

A mixture of 20 g of 1-(3,4-methylenedioxyphenyl)-1-pentene-3-one (0.1 mole), 3 g of paraformaldehyde (0.1 mole) and 12.2 g of morpholine hydrochloride (0.1 mole) in 100 cm³ of absolute alcohol adjusted to a pH of 3 is refluxed for 9 hours. The alcohol is removed and the product is taken up in water. The product is then extracted with chloroform, and the basic, aqueous phase is taken and re-extracted with benzene. A yellow oil is obtained which can be used for the reduction of Example 6.

Yield 40%. (Hydrochloride recrystallised in absolute ethanol, M.P.=209°).

EXAMPLE 6

1-(3,4-methylenedioxyphenyl)-4-methyl-5-morpholino-1-pentene-3-ol (Code No.: 1156)

The same technique as in Example 1 is used, starting with the compound of Example 5. Extraction with chloroform. Recrystallisation from ethanol.
M.P.=89°, Yield=80%.
M.P. (hydrochloride)=250°.

EXAMPLE 7

1-(3,4-methylenedioxyphenyl)-4-piperidino-1-butene-3-ol (Code No.: 1448)

(a) 1-(3,4-methylenedioxyphenyl)-4-piperidino-1-butyne-3-one.

14.6 g of 3,4-methylenedioxyphenylacetylene (0.1 mole) is added to a solution of ethyl-magnesium bromide (0.1 mole) prepared from 10.9 g of ethyl bromide and 2.4 g of magnesium. After refluxing for 2 hours while stirring, 12.4 g of 2-piperidinoacetonitrile (0.1 mole) is added. The mixture is refluxed for 4 hours and left overnight, and is then decomposed and hydrolysed with a saturated solution of $NH_4Cl$. The solution is extracted with ether, 10% HCl, the aqueous phase is made alkaline, and is re-extracted with benzene.

The product is recrystallised from petroleum ether.
M.P.=56°, Yield=55%.

(b) 1-(3,4-methylenedioxyphenyl)-4-piperidino-1-butene-3-ol.

The acetylenic ketone (27 g, 0.1 mole) obtained above is dissolved in anhydrous ether. An ethereal suspension of $LiAlH_4$ (0.2 mole) is added and the reaction mixture is refluxed for 8 hours. The mixture is decomposed with water, then extracted with ether, and is finally recrystallised from diisopropyl oxide (M.P.=82°). The hydrochloride of the compound obtained is prepared and recrystallised from an ethanol-acetone mixture (50-50).
M.P.=192° (instantaneous), Yield: 50%.

The compounds of the preceding examples as well as other compounds prepared in a similar manner are given in Table I below.

TABLE I

| Code No. | Formula | M.P. (°C.) base | M.P. (°C.) hydrochloride (recrystallisation solvent) |
|---|---|---|---|
| 996 | [3,4-methylenedioxyphenyl]—CH=CH—C(=O)—CH$_2$—N(morpholino) | 105° (ethanol) | 235° |
| 998 | [3,4-methylenedioxyphenyl]—CH=CH—C(=O)—CH$_2$—CH$_2$—CH=C(CH$_3$)$_2$ | 66° (ethanol) | |
| 1003 | [3,4-methylenedioxyphenyl]—CH=CH—C(=O)—CH=C(CH$_3$)$_2$ | 90° (ethanol) | |
| 1036 | [3,4-methylenedioxyphenyl]—CH=CH—C(=O)—cyclohexyl | 67° (ethanol) | |
| 1201 | [3,4-methylenedioxyphenyl]—CH=CH—C(=O)—CH(CH$_3$)—CH$_2$—N(piperazino)N—CH$_3$ | | 214° (2 HCl) (ethanol) |
| 1321 | [3,4-methylenedioxyphenyl]—CH=CH—C(=O)—CH(CH$_3$)—N(morpholino) | 75° (ethanol) | 208° (ethanol + ether) |
| 1156 b | [3,4-methylenedioxyphenyl]—CH=CH—C(=O)—CH(CH$_3$)—CH$_2$—N(morpholino) | — (oil) | 209 |

TABLE I-continued

| Code No. | Formula | M.P. (°C.) base (recrystallisation solvent) | M.P. (°C.) hydrochloride (recrystallisation solvent) |
|---|---|---|---|
| 997 | 3,4-methylenedioxyphenyl-CH=CH-CH(OH)-CH$_2$-N(morpholino)·HCl | 108° (ethanol) | 162° (ethanol) |
| 999 | 3,4-methylenedioxyphenyl-CH=CH-CH(OH)-CH$_2$-CH$_2$-CH=C(CH$_3$)$_2$ | 52° (petroleum ether) | |
| 1037 | 3,4-methylenedioxyphenyl-CH=CH-CH(OH)-cyclohexyl | 60° (cyclohexane) | |
| 1156 | 3,4-methylenedioxyphenyl-CH=CH-CH(OH)-CH(CH$_3$)-CH$_2$-N(morpholino) | 89° (ethanol) | 250° inst. (ethanol) |
| 1202 | 3,4-methylenedioxyphenyl-CH=CH-CH(OH)-CH(CH$_3$)-CH$_2$-N(N'-methylpiperazino) | 84° (diisopropyl ether) | 270° inst. 2HCl (ethanol) |
| 1340 | 3,4-ethylenedioxyphenyl-CH=CH-CH(OH)-CH(CH$_3$)-N(morpholino) | 114° (ethanol 50 water 50) | unstable |
| 1448 | 3,4-ethylenedioxyphenyl-CH=CH-CH(OH)-CH$_2$-N(piperidino) | 82° | 192° (inst.) |
| AB 753 | 3,4-ethylenedioxyphenyl-CH=CH-C(O)-CH$_2$-CH$_2$-CH$_2$-N(piperidino) | 67° | 224° (inst.) |
| AB 754 | 3,4-ethylenedioxyphenyl-CH=CH-CH(OH)-CH$_2$-CH$_2$-CH$_2$-N(piperidino) | Liquid $n_D^{25}$ = 1,5520 | 174° (ethanol) hygroscopic |
| 1447 | 3,4-methylenedioxyphenyl-CH=CH-C(O)-CH$_2$-N(piperidino) | 62° (cyclohexane) | 218° (ethanol) |
| 1451 | 3,4-methylenedioxyphenyl-CH=CH-C(O)-CH$_2$-N(N'-methylpiperazino) | 70° (ethanol) | 218° (ethanol) |
| 1491 | 3,4-methylenedioxyphenyl-CH=CH-CH(OH)-CH$_2$-N(N'-methylpiperazino) | 82° | 180° (ethanol) |

TABLE I-continued

| Code No. | Formula | M.P. (°C.) base | M.P. (°C.) hydrochloride (recrystallisation solvent) |
|---|---|---|---|
| 1449 | ![structure] O—⟨benzene⟩—CH=CH—C(=O)—CH$_2$—CH$_2$—CH$_2$—N⟨morpholine⟩ (with methylenedioxy) | 90° | 234° |
| 1450 | O—⟨benzene⟩—CH=CH—CH(OH)—CH$_2$—CH$_2$—CH$_2$—N⟨morpholine⟩ (with methylenedioxy) | 52° | 174° |

The compounds of the invention have undergone pharmacological tests.

A. Toxicity

The $LD_{50}$ of the products was measured in mice by the intraperitoneal route in accordance with the "Log-Probits" method of Miller and Tainter (Proc. Soc. Exptl. Biol. Med. 1944; 57, 261-264).

B. Activity on the central nervous system

This was investigated by observing the behaviour of animals, by studying the modifications in narcosis produced by hexobarbital and studying the anti-convulsant power.

1. Modification of narcosis produced by hexobarbital

Mice, each weighing about 20 g, received the product under investigation by the intraperitoneal route. Half an hour later sodium hexobarbital was injected by the same route at a dosage of 70 mg/kg.

The animals were placed on a hot plate kept at a constant temperature of 27° C. It is considered that sleep is established when a mouse, placed in the dorsal decubitus, is incapable of turning over and standing on its paws.

The narcosis potentialisation is evaluated by the percentage increase in sleeping time induced by hexobarbital (T).

2. Anti-convulsant action (Boissier—Actualités Pharmacologiques, Series 12, page 1)

(a)—Attack caused by pentetrazol.

A convulsive attack is caused by pentetrazol which, when injected into mice intraperitoneally at a dosage of 125 mg/kg, produces 100% mortality in 5 to 7 minutes.

Mice, each weighing about 20 g, are given the product being studied intraperitoneally, thirty minutes before the administration of pentetrazol. The time of death is determined compared with that (t) of the control group that did not receive the product, as well as the percentage protection (P).

(b)—Electric shock.

The application of an electric current of 30 volts for 0.5 second to the cerebral hemispheres produces an epileptic attack.

Male rats each weighing 180 to 200 g receive intraperitoneally the solvent or the product being investigated. Thirty minutes later the animals are subjected to electric shocks. It is noted whether the attack is complete or incomplete, and the percentage protection (P) conferred by the product administered is determined.

3. Antagonism to reserpine (Blepharospasm)

(Chen G., and Bohner B., (1961) J. pharmacol. Exptl. Therap. 131, 179).

Reserpine administered to mice in a dosage of 5 mg/kg intraperitoneally produces in the first few hours a more or less complete closure of the eyelids in most of the animals. The administration of certain products inhibits the blepharospasm caused by reserpine.

Male Swiss mice are distributed into batches of 10 mice and each experiment involves at least 3 batches:
- a control batch that receives only the solvent and reserpine
- a batch treated with a reference product: we selected Imipramine
- a treated batch receiving the product being tested.

The experimental products are administered intraperitoneally either 30 minutes or 2 hours before the intraperitoneal injection of reserpine at a dosage of 5 mg/kg, in order to study their activity as a function of time.

The degree of ptosis for each eye and each animal is observed every 30 minutes for 4 to 5 hours, using RUBIN's score method. The activity of the product is determined by comparison with the result obtained with the treated control batch. The inhibition of blepharospasm is marked from 0 to +++.

The results obtained in these various tests are given in table II below.

TABLE II

| Code No. | $LD_{50}$ (mg/kg) IP | Narcosis potentialisation mg/kg | | Pentrazole IP mg/kg | | Electric shock IP mg/kg | | blepharospasme IP mg/kg | |
|---|---|---|---|---|---|---|---|---|---|
| | | | T | | | | | | |
| 996 | 750 | 75 | 106% | 75 | P = 0 | 75 | P = 50% | 75 | + |
| 998 | 2000 | 200 | 490% | 200 | P = 0 | 200 | P = 30% | 200 | 0 |
| 1003 | 2000 | 200 | 223% | 200 | P = 0 | 200 | P = 0 | 200 | 0 |
| | | | | | t × 15 | | | | |
| 1036 | 2000 | 200 | 135% | 200 | P = 10% | 200 | P = 0 | | |

TABLE II-continued

| Code No. | LD$_{50}$ (mg/kg) IP | Narcosis potentialisation mg/kg T | | Pentrazole IP mg/kg | | Electric shock IP mg/kg | | blepharospasme IP mg/kg |
|---|---|---|---|---|---|---|---|---|
| 1201 | 75 | 7.5 | 17% | 7.5 | t × 2.6 P = 0 | 7.5 | P = 10% | 7.5 | ± |
| 1321 | 850 | 85 | 227% | 85 | t × 2 P = 20 | 85 | P = 50% | 85 | 0 |
| 997 | 500 | 50 | 0 | 50 | P = 0 | 50 | P = 60% | 50 | +++ |
| 999 | 1000 | 100 | 201% | 100 | t × 2 P = 0 | 100 | P = 90% | 50 | 0 |
| 1037 | 1000 | 100 | 225% | 100 | t × 5 P = | 100 | P = 0 | | |
| 1156 | 600 | 60 | 79% | 60 | P = 10% | 60 | P = 50% | 60 | 0 |
| 1202 | 250 | 25 | 5% | 25 | t × 1.6 P = 10% | 25 | P = 10% | 25 | 0 |
| 1340 | 400 | 40 | 23% | 40 | t × 2 P = 10% | 40 | P = 10% | 40 | ± |

As can be seen from the results of the pharmacological tests described above, the compounds of the invention act on the central nervous system, so that they can be used for treating nervous and psychosomatic disorders.

They may be used in particular as tranquilisers, anticonvulsants and anti-depressants. The compounds Nos. 997 and 996 have been found to be particularly useful as anti-depressants.

The compounds of the invention may be formulated in combination with a pharmaceutically compatible excipient for oral administration, for example in the form of tablets, pills or capsules, for parenteral administration in the form of solutions for injection, or for endorectal administration in the form of suppositories.

The daily dosage will be of the order of 50 to 300 mg orally, and, where necessary, 5 to 50 mg by injection for the soluble compounds (amine salts).

We claim:
1. The compound 1-(3,4-methylenedioxyphenyl)-4-morpholino-1-butene-3-ol or a pharmaceutically acceptable salt thereof.
2. The compound of claim 1 in the form of the hydrochloride salt.
3. A pharmaceutical agent capable of treating nervous and psychosomatic disorders which comprises effective amount of a compound of claim 1 for treating said nervous and psychosomatic disorders and a compatible pharmaceutical acceptable carrier.
4. A method of combatting nervous and psychosomatic disorders in a patient which comprises administering to said patient said pharmaceutical agent of claim 3.
5. A method of treating depression in a patient which comprises administering to said patient an effective amount of the compound of claim 1.

* * * * *